(12) United States Patent
Weiss

(10) Patent No.: US 6,501,546 B1
(45) Date of Patent: Dec. 31, 2002

(54) INSPECTION SYSTEM FOR EDGES OF GLASS

(75) Inventor: Adam Weiss, Pickering (CA)

(73) Assignee: Photon Dynamics Canada Inc., Markham (CA)

( * ) Notice: Subject to any disclaimer, the term of this patent is extended or adjusted under 35 U.S.C. 154(b) by 0 days.

(21) Appl. No.: 09/568,238

(22) Filed: May 5, 2000

(51) Int. Cl.[7] .................................................. G01N 21/88
(52) U.S. Cl. .................................. 356/239.1; 356/239.7
(58) Field of Search .......................... 356/239.1, 239.2, 356/239.7, 237.1, 614, 622, 624; 250/559.29, 559.36, 559.42, 559.45, 559.46, 559.49

(56) References Cited

U.S. PATENT DOCUMENTS

| | | | |
|---|---|---|---|
| 3,737,665 A | 6/1973 | Nagae | |
| 4,492,477 A | 1/1985 | Leser | |
| 4,583,854 A | 4/1986 | Lozar | |
| 4,641,966 A | 2/1987 | Lemmers et al. | |
| 5,406,048 A | * 4/1995 | Yamazaki et al. | 219/121.78 |
| 5,459,330 A | 10/1995 | Venaille et al. | |
| 6,011,620 A | 1/2000 | Sites et al. | |

FOREIGN PATENT DOCUMENTS

| | | |
|---|---|---|
| CA | 2252308 | 10/1998 |
| DE | 3926349 A1 | 8/1989 |
| DE | 41 39 094 | 11/1991 |
| DE | 198 09 505 | 3/1998 |
| EP | 0 317 638 | 5/1989 |
| EP | 0 559 916 | 9/1992 |
| GB | 1 526 930 | 12/1974 |
| WO | WO 96/05503 | 2/1996 |
| WO | WO 00/26647 | 5/2000 |

OTHER PUBLICATIONS

Patent Abstracts of Japan, publication No. 04157344.
Patent Abstracts of Japan, vol. 1997, No. 04, Apr. 30, 1997, for: JP 08 327561 A, Dec. 13, 1996.
Patent Abstracts of Japan, vol. 016, No. 468, Sep. 29, 1992, for: JP 04 168251, Jun. 16, 1992.
Patent Abstracts of Japan, vol. 1996, No. 11, Nov. 29, 1996, for: JP 08 193955, Jul. 30, 1996.
International Search Report for: PCT/CA99/00953, completed: Dec. 20, 1999.

* cited by examiner

*Primary Examiner*—Hoa Q. Pham
(74) *Attorney, Agent, or Firm*—Merchant & Gould P.C.

(57) ABSTRACT

An inspection system for the edge of a sheet of glass e.g. automobile glass. The system has at least one laser, with the laser beam directed at the edge of the glass. Light reflected from the edge is recorded e.g. with a camera. The path length from the laser to the glass edge and back to the camera is maintained constant as the glass moves through the apparatus.

42 Claims, 7 Drawing Sheets

INSPECTION SYSTEM FOR EDGES OF GLASS

FIELD OF THE INVENTION

The present invention relates to a non-contact inspection system for detection and identification of defects on the edges of sheets of glass, especially the edges of flat automotive glass. The system is intended to operate on a continuous production line at line speed, and to be used for detection and identification of a wide variety of types of defects, including chips, cracks, poor grinding and other edge defects.

BACKGROUND OF THE INVENTION

In processes for manufacture of glass in sheet form, it is necessary to be able to inspect the sheets of glass for defects. Such defects may be in the form of scratches, bubbles, chips, blemishes and a wide variety of other defects. In addition, the manufacturer of the sheet glass needs to know whether the defects are insignificant e.g. minor in nature and thus acceptable to the customer, or significant such that the sheet of glass would not conform to specifications established by the customer. It is important to able to conduct the inspection on-line in the production process, at production speeds, so that defects may be rapidly identified and communicated to production personnel and/or the sheets of glass with the defects may be readily and quickly separated from sheets of glass meeting quality specifications in an effective manner.

Methods have been developed for the inspection of sheets of glass using optical techniques. Apparatus and a method that are particularly intended for use in inspection of sheets of glass in a production line, at production speeds, in a manner that shows the magnitude, type and location of the defects in the sheets of glass are disclosed in Canadian Patent Application No. 2252308 of Adam Weiss and Alexandre Obotnine filed Oct. 30, 1998. Such apparatus and method, referred to herein as viewing area apparatus, are especially intended to be an integral part of a glass processing system.

The aforementioned Canadian Patent Application No. 2252308 is directed to a method for the inspection of sheets of glass, in which the sheets of glass are transported through the beams of lasers. Such an inspection is intended to detect bubbles and other defects in the sheets of glass but not defects on the edges of the sheets of glass except to the extent that those defects extend from the edges of the sheets of glass into the sheets of glass. The lasers are not in a position to inspect the edges of the sheets of glass.

Detection of defects on the edges of the sheets of glass is also important, as such defects may affect both visual and physical properties of the sheets of glass.

SUMMARY OF THE INVENTION

Apparatus and a method have now been found for inspection of the edges of sheets of glass in a production line, at production speeds, especially in a manner that shows the magnitude, type and location of the defects.

Accordingly, one aspect of the present invention provides an inspection system for the edge of a sheet of glass, comprising:

a) means to support and move a sheet of glass in a plane in a first direction, said means to support and move the sheet of glass maintaining the glass in a constant plane;

b) a laser that provides a beam of laser light;

c) an optical recording device for said laser beam;

d) means to direct the laser beam onto said edge of the sheet of glass at an angle to said first direction and to direct light reflected therefrom to said optical recording device, the light reflected from the edge of the sheet being coaxial with light directed onto the edge of the sheet; and e) means to control the total path length of said laser beam from said laser to said edge and from said edge to said optical recording device at a substantially constant length.

In preferred embodiments of the apparatus of the present invention, the system additionally comprises software that utilizes information from the light detection system to determine the location, type and magnitude of defects in the edges of the sheet of glass.

In a further embodiment, the system additionally has means to record the location, type and magnitude of defects in the edges of the sheets of glass, optionally including a display or a defect map, especially a defect map displayed on a screen.

Another aspect of the present invention provides a method for the inspection of the edge of a sheet of glass, comprising:

a) supporting and moving a sheet of glass in a plane in a first direction, said sheet of glass being maintained in a constant plane;

b) directing a laser beam onto said edge of the sheet of glass at an angle to said first direction and directing light reflected therefrom to an optical recording device, the light reflected from the edge of the sheet being coaxial with light directed onto the edge of the sheet; and e) controlling the total path length of said laser beam from said laser to said edge and from said edge to said optical recording device at a substantially constant length.

BRIEF DESCRIPTION OF THE DRAWINGS

The present invention is illustrated by the embodiments shown in the drawings, in which.

DETAILED DESCRIPTION OF THE INVENTION

Techniques for the manufacture of glass are known. For example, glass may be converted to a molten state and then cast onto molten tin metal so that glass with a smooth surface may be obtained. Nonetheless, the glass that has been cast may be subject to a number of defects, including the presence of bubbles, dirt, stones, tin-drip distortion and other defects. Some such defects might arise from raw materials fed to the process while other defects will arise from processing problems, including incorrect temperature or other process parameters and ageing of the glass forming apparatus, especially of kilns or other apparatus used in the heating of the glass.

Subsequent to the casting of the glass, the glass is cut into sheets and then transferred to a manufacturer of glass articles for a particular end-use. In the automobile industry, for instance, the glass articles could be the windows of the vehicle, in which event the manufacturer will shape the sheets of glass to a particular size and configuration, prepare ground edges to the glass, cut holes in the glass in locations as required, imprint logos or other writing in the glass and otherwise process the cut glass to a predetermined set of specifications. Despite care in operation of the process, the various steps can result in the formation of chips, cracks, scratches, and other defects that might render the glass unacceptable to a customer. The manufacturer must be able to detect the defects, and separate sheets of glass conforming to specification from those that do not.

As noted above, one of the steps in the manufacture of a sheet of glass is the preparation of ground edges to the sheet of glass. The step of grinding may result in a number of defects in an edge of the sheet of glass, including shiners viz. sections of the edge of the glass that have not been ground, open shiners viz. shiners in which the section of un-ground glass extends into the top of the sheet of glass, edge chips, V-chips and burns viz. sections of glass that were over-heated during the grinding process.

Some of these defects could be a result of defects in the edge of the glass prior to grinding that were not removed in the grinding step. Other defects are the result of the grinding step per se e.g. a mis-aligned grinding wheel, a grinding wheel that has become worn out and/or which causes overheating, or other grinding difficulties.

While the glass is generally described herein as a sheet of glass, it is to be understood that in many instances the glass is in the form of a laminated or tempered glass or other glass, to give it strength, shatter resistance or other properties. The processes used to form such glass may add to the potential defects in the edge of the sheet of glass.

Figure 1:
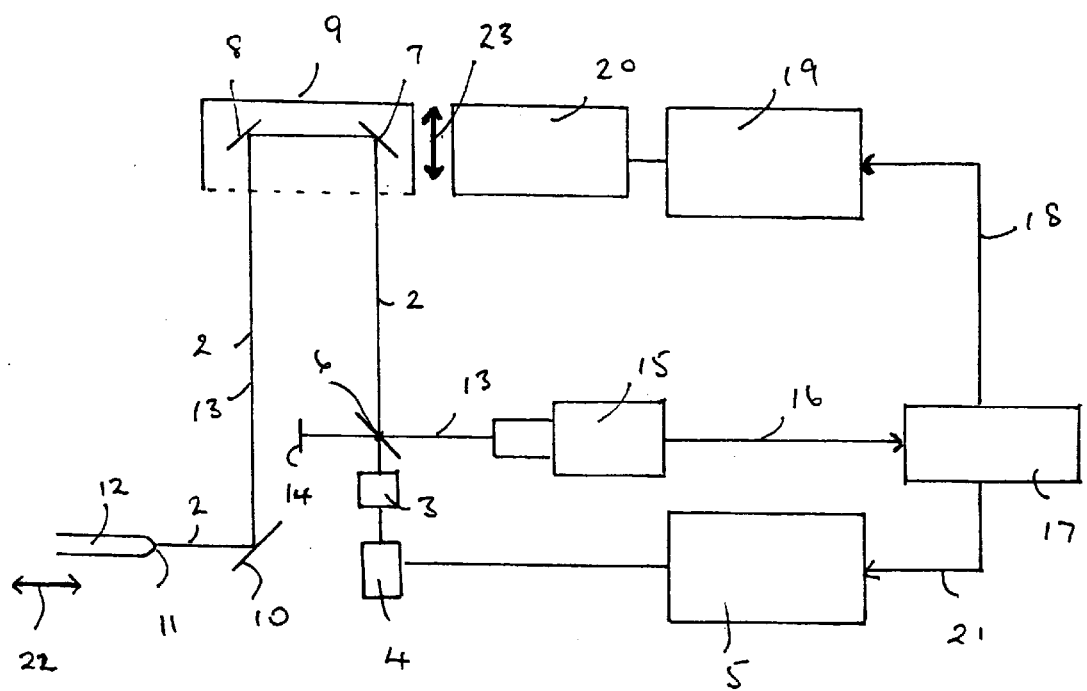
FIG. 1 is a schematic representation of a glass edge inspection apparatus of the present invention.

FIG. 1 shows a schematic representation of an inspection system 1 for edges of glass in accordance with the present invention. Apparatus 1 has a laser 3 that generates a laser beam 2. Laser 3. is controlled by laser controller 4 and laser power control 5. Laser beam 2 passes through beam splitter 6 and is reflected by mirrors 7 and 8 in moveable head 9. Laser beam 2 is further reflected at mirror 10 onto edge 11 of glass sheet 12.

Light from edge 11 is reflected back to mirror 10 as reflected beam 13. The light reflected from edge 11 of glass sheet 12 is coaxial with the laser beam 2 directed onto edge 11 of glass sheet 12. Reflected beam 13 then passes to mirrors 8 and 7 in moveable head 9 and to beam splitter 6. At beam splitter 6, reflected beam 13 passes to an imager or camera 15, which may be in the form of a high-resolution photodiode CCD (charged coupled device) TDI (time delayed integration) device. Camera 15 communicates with computer 17 through cable 16.

Computer 17 additionally controls stepping motor control 19 by means of cable 18, which in turn controls motion mechanism 20. Computer 17 further communicates with laser power control 5 through cable 21.

Glass edge 11 will undergo lateral movement, as indicated at 22, during inspection of the glass edge, as discussed below. Moveable head 9 will undergo movement in a vertical direction i.e. a direction perpendicular to the movement of glass edge 1 1, as indicated at 23.

In operation, a sheet of glass 12 is transported into the apparatus for inspection of the edge of the glass. The presence of the glass, and the position of the glass is detected, as is discussed below. Computer 17 activates laser 3 so that laser beam 2 is passed to mirrors 7, 8 and 10 and directed at glass edge 11. It is important that laser beam 2 be in the plane of the sheet of glass 12. As laser beam 2 is at an angle to the direction of travel of sheet of glass 12, laser beam 2 will contact edge 11 at varying positions as sheet of glass 12 moves, traversing along edge 11. If laser beam 2 and edge 11 are not in the same plane i.e. not aligned, then laser beam 2 will not always be in contact with edge 11.

Reflected beam 13 passes back from mirror 10 to mirrors 8 and 7 and is redirected at beam splitter 6 to camera 15. Camera 15 communicates with computer 17, so that computer 17 obtains a record of the images reflected from glass edge 11.

As is discussed herein, laser beam 2 is normally not directed at an angle that is perpendicular to glass edge 11. In particular, laser beam 2 is directed from mirror 10 towards glass edge 11 at an angle to the direction of travel of glass sheet 12. As glass sheet 12 is continuously moved through apparatus 1, the distance from mirror 10 to glass edge 11 is constantly varying. During the inspection process, the distance between glass edge 11 and mirror 10 will increase and decrease as each sheet of glass passes through the inspection apparatus. The constantly varying position of the edge of the glass would result in varying intensity and magnification of the reflected beam 13 that passes from glass edge to camera 15, even if there were no changes in the reflected properties of glass edge 11. This causes variations in the intensity of the light and magnification of the image that would be recorded at camera 15. If defects are present on glass edge 11, such variations in light intensity and magnification caused by the varying distance of glass edge 11 from mirror 10 may result in variations and masking of defects that are present on glass edge 11.

To overcome the problem of varying intensity and magnification caused by the varying position of glass edge 11 as sheet glass 12 is inspected, the location of glass edge 11 is detected and predicted using computer 17. Computer 17 then varies the position of moveable head 9 using an adjustment mechanism that includes step motor control 19 and motion mechanics 20. In particular, moving head 9 is moved in a direction perpendicular to the movement of glass sheet 12 so that the distance from laser 2 to glass edge 11 and back to camera 15 is maintained substantially constant. As used herein, "substantially constant" means maintaining the light received by the camera in focus i.e. within the depth of field of focus of the camera. In embodiments, the depth of field may be ±30 mm.

At beam splitter 6, light passing through is split, with part of the light being directed to laser light trap 14.

Figure 2:
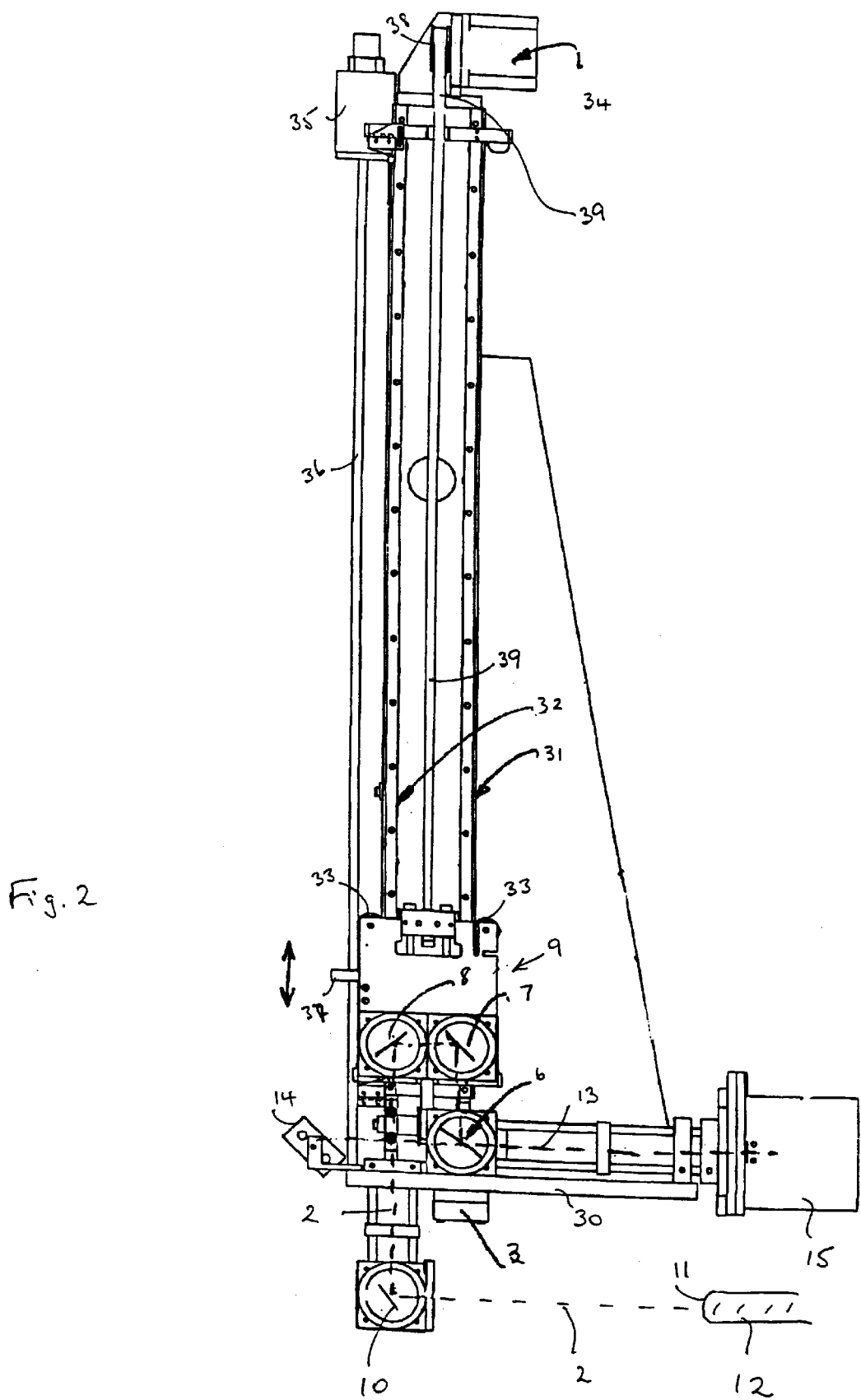
FIG. 2 is a schematic representation of a side view of the glass edge inspection of apparatus of FIG. 1.

FIG. 2 shows a side, partly in section, view of apparatus 1. Laser 3 is located on frame 30, which also houses beam splitter 6. Camera 15 is located on one end of frame 30, with laser light trap 14 located on the opposed end. Beam splitter 6 is intermediate therebetween. Mirrors 7 and 8 are located within moveable head 9, which is shown at the bottom of rails 31 and 32 that extend perpendicular with respect to glass sheet 12. Moveable head 9 moves along rails 31 and 32 on wheels 33, two of which are shown.

Stepping motor 34 is located at the upper end of rails 31 and 32. Stepping motor 34 drives pulley 38 around which passes belt 39. Belt 39 extends downwards and is attached to moveable head 9; belt 39 is further shown and described in FIGS. 3 and 4. Guide bar 36 extends from absolute displacement transducer 35 parallel to rails 31 and 32, passing through guide 37. Absolute displacement transducer 35 is used to determine the vertical position of moveable head 9.

In operation, stepping motor 34 is controlled by computer 17 (not shown in FIG. 2). Stepping motor 34 causes pulley 38 to rotate in a clockwise or anticlockwise direction, which causes corresponding movement in belt 39. Consequently, moveable head 9 is raised or lowered along rails 31 and 32. Stepping motor 34 is controlled so that the total path length of laser beam 2, from laser 3 through beam splitter 6, past mirrors 7, 8 and 10 to glass edge 11 and of reflected beam 13 back through mirrors 10, 8, 7 and beam splitter 6 to camera 15 is maintained substantially constant.

Figure 3:
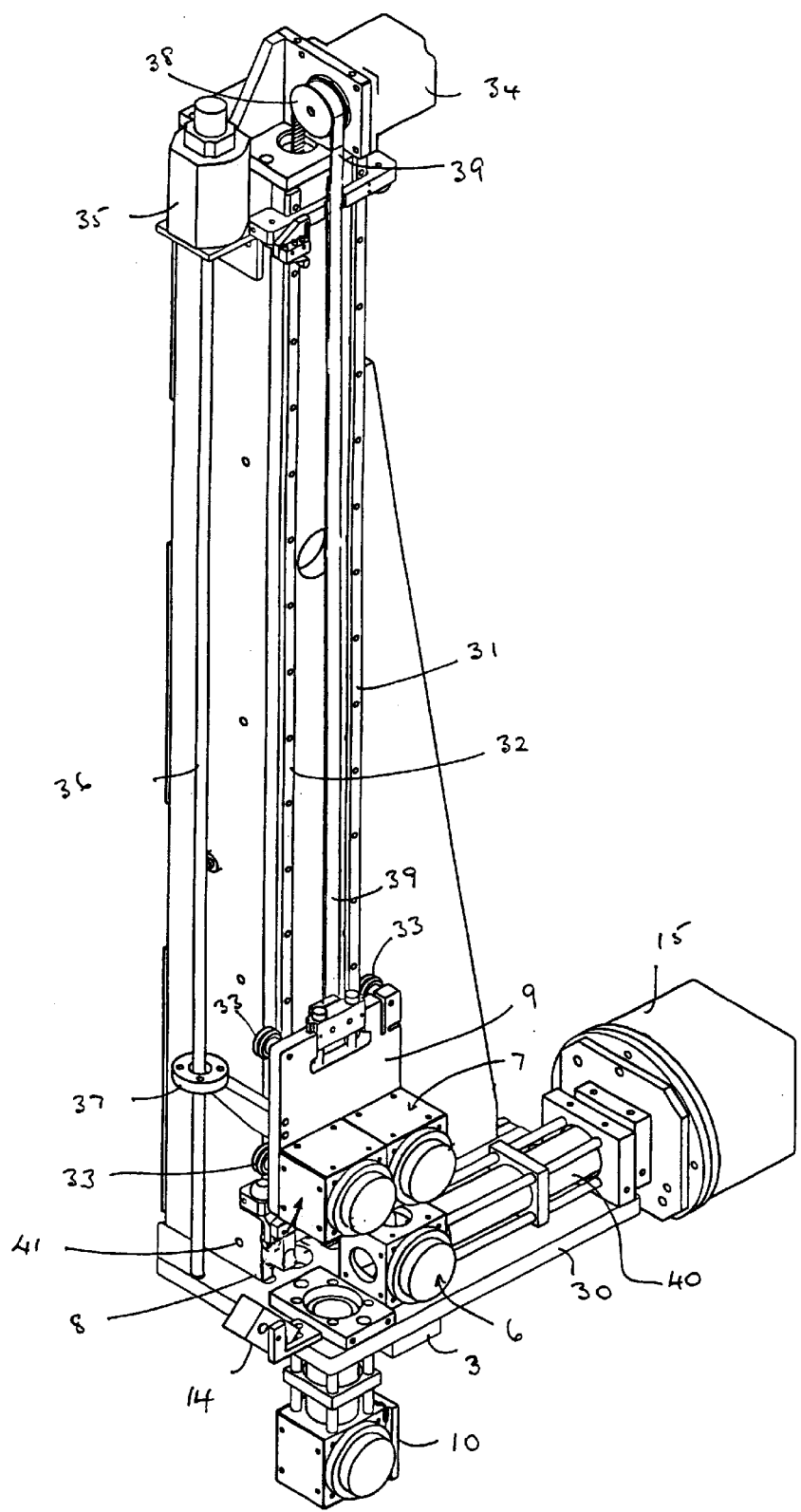
FIGS. 3 and 4 are schematic representations of perspective views of the glass edge inspection system of FIG. 1.
Figure 4:
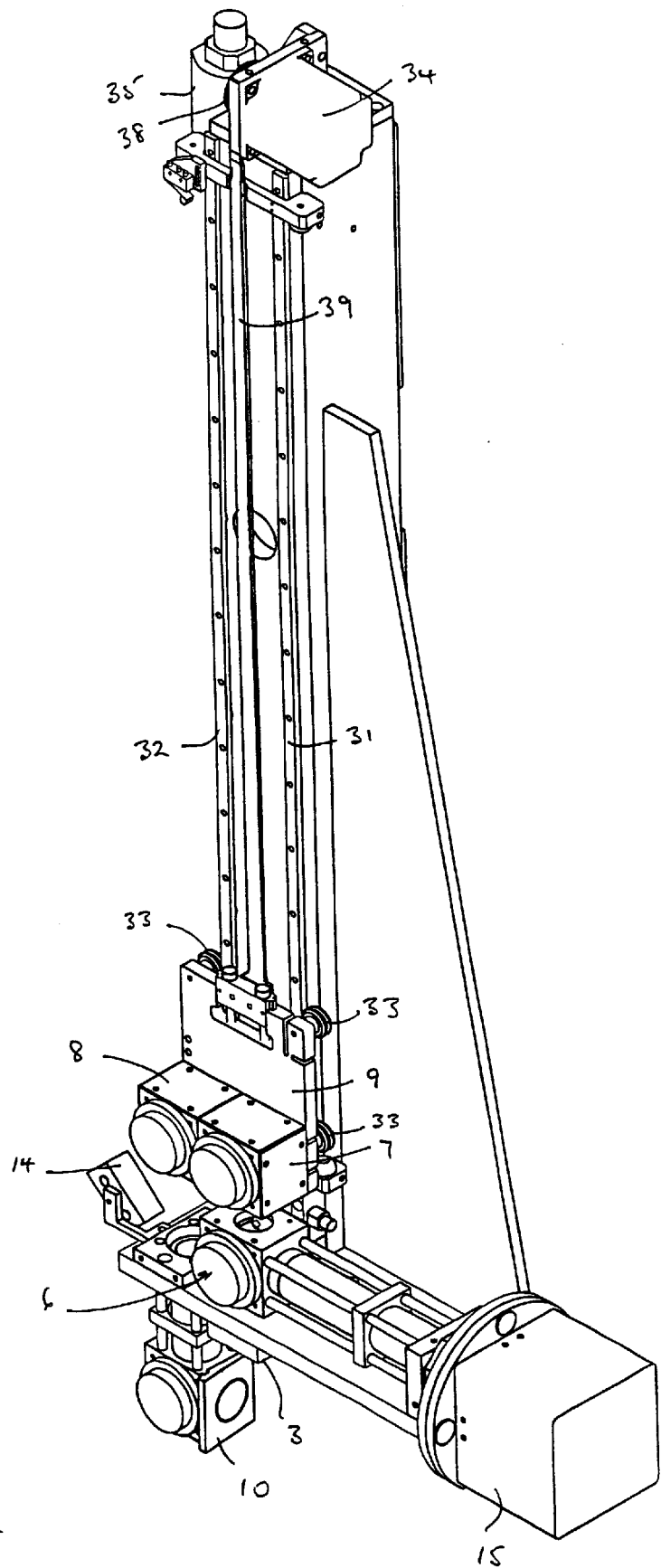

FIGS. 3 and 4 show camera 15 located on frame 30 and connected to beam splitter 6 by enclosed tube 40, through which reflected beam 13 passes. Mirrors 7 and 8 are shown as enclosed in housings, which are attached to moveable head 9. Mirror 10 as also shown as being enclosed.

Belt 39, which is shown as being a stepped belt, passes around pulley 38 of stepped motor 34 and extends downwards to moveable head 9. Although not apparent in FIG. 3, belt 39 also extends downwards from pulley 39 behind the frame of rails 31 and 32, around spindle 41 and is attached to moveable head 9. Thus, rotation of pulley 39 effects vertical movement of moveable head 9.

Figure 5:
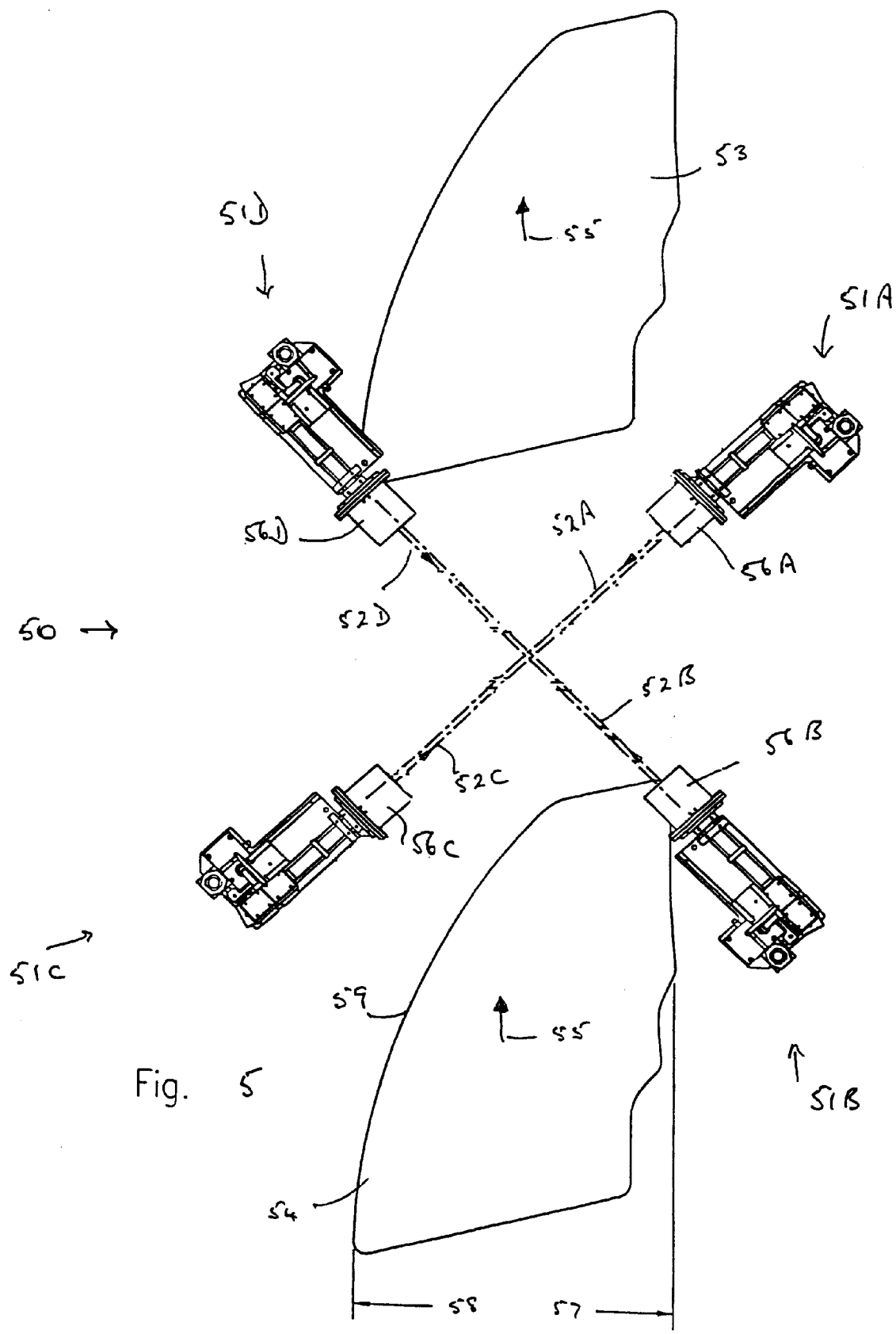
FIG. 5 is a schematic representation of a plan view of four units of glass edge inspection apparatus.

FIG. 5 shows a plan view of a glass inspection apparatus 50 with four units for inspection of edges of glass. Two sheets of glass 53 and 54 are represented. All support and transportation structure has been omitted for clarity. Apparatus 50 has four units for inspection of edges, being units 51A–51D. Units 51A–51D are disposed at approximately the corners of a rectangle, with units 51 A and 51C at opposed ends of one diagonal and units 51B and 51D at opposed ends of the other diagonal. Units 51A and 51C are shown as being aligned, so that the laser beam 52A from unit 51A is directed at and detected by unit 51C, and vice versa. In this manner, the units can detect the presence or absence of glass between the units. Units 51B and 51D are similarly aligned. However, in addition, the position and orientation of the sheet of glass should be determined prior to the sheet of glass entering the inspection apparatus, so that the computer can predict arrival of the sheet of glass and adjust the mirror position, as discussed herein.

Laser beams 52A–52D are aligned in the plane of sheets of glass 53, 54 that are transported horizontally passed units 51A–51D, in the direction of arrows 55. The mechanism for transporting sheets of glass 53 and 54 is not shown in FIG. 5.

Cameras 56A–56D are located above the plane of the sheets of glass. Outer edges 57,58 of glass sheet 54 pass under cameras 56A–56D but in a position such that laser beams 52A–52D will contact glass edge 59 as glass sheet 54 passes by units 51A–51D.

Glass sheet 54 is of an irregular shape, but such shape is typical of a window for an automobile. As glass sheet 54 passes laser beams 52A–52B, all of edge 59 of glass sheet 54 is traversed at least once by a laser beam. It is important that laser beams 52A–52B be at an angle to the direction of travel 55 in order that all of edge 59 is traversed by at least one laser beam.

Figure 6:
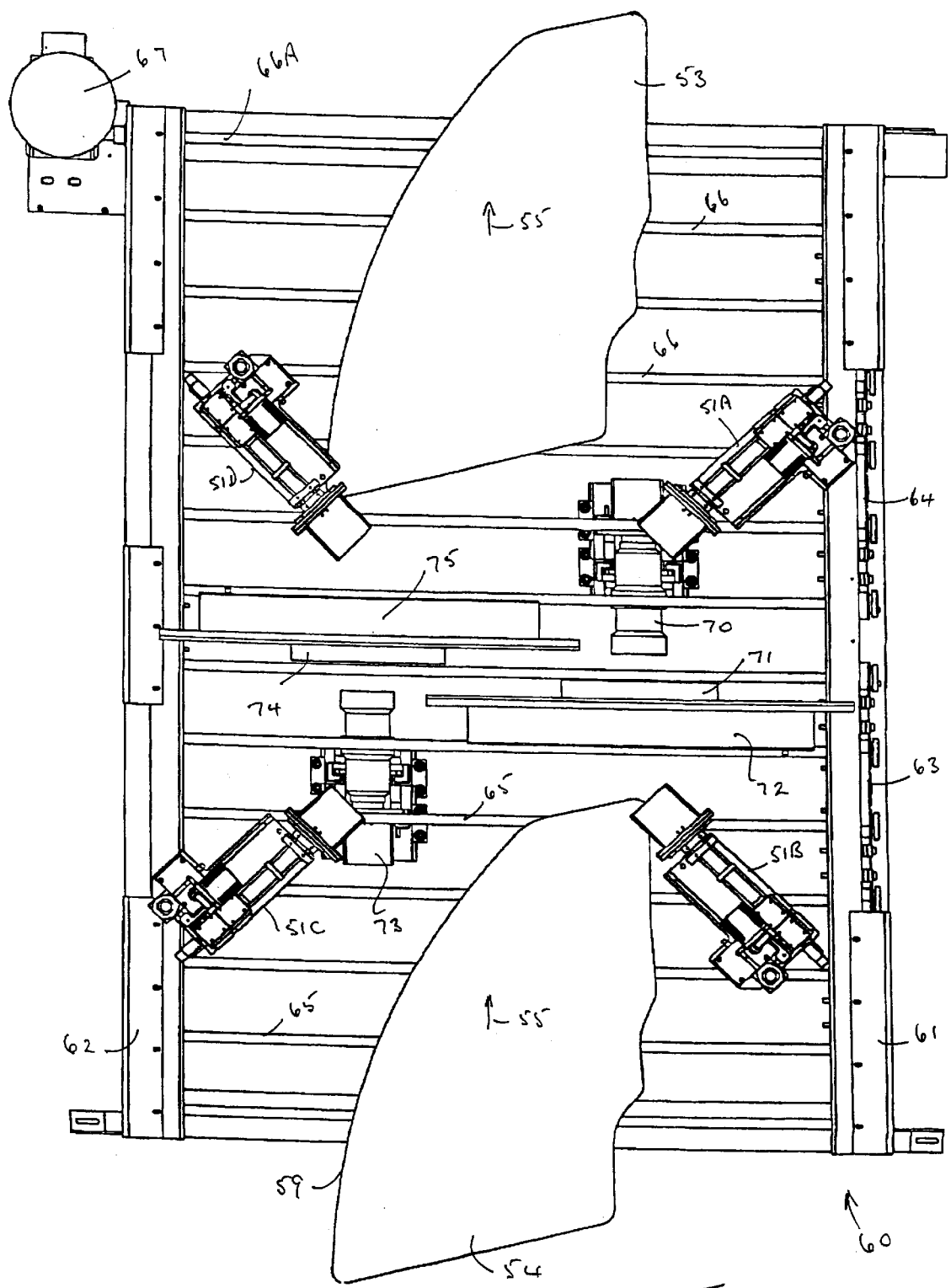
FIG. 6 is a schematic representation of the plan view of FIG. 5 with accompanying structure.

FIG. 6 shows a plan view of the glass edge inspection apparatus of FIG. 5 with accompanying structure. Glass sheets 53 and 54 are shown as being on support 60. Support 60 has frame sides 61 and 62. Frame side 61 accommodates drive mechanisms 63 and 64, which are more clearly seen in FIG. 7. Drive mechanisms 63 and 64 are partially enclosed. Drive mechanism 63 rotates rollers 65 that extend between frame sides 61 and 62. Similarly, drive mechanism 64 rotates rollers 66 that also extend between frame sides 61 and 62. Rollers 65 and 66 are rotated at the same constant speed, and transport glass sheets 53 and 54 through the edge inspection apparatus 50.

One of rollers 66 viz. roller 66A, is directly driven by motor 67, roller 66A in turn effecting rotation of the remainder of rollers 66 by means of drive mechanism 64. A belt (not shown) extends along and within frame side 62 to rotate one of the rollers 65, which in turn effects rotation of the remainder of rollers 65 by means of drive mechanism 63. Thus, rotation of rollers 65 and 66 may be maintained at a constant speed.

FIG. 6 shows viewing area cameras 70 and 73 for inspection of the sheet of glass for bubbles, scratches, chips, blemishes and other defects, as disclosed in the aforementioned Canadian patent application of Weiss and Obotnine. Such inspection of the sheet of glass may be and preferably is carried out simultaneously with the glass edge inspection. Viewing area camera 70 has mirror 71 and light source 72. Similarly, viewing area camera 73 has mirror 74 and light source 75. Two viewing area cameras, 70 and 73, are used so that the full width of glass sheets 53,54 may be inspected.

Units 51A–51D have been described above. It is understood that suitable structure for support of units 51A–51D would be required. Such structure has been omitted for clarity.

Figure 7:
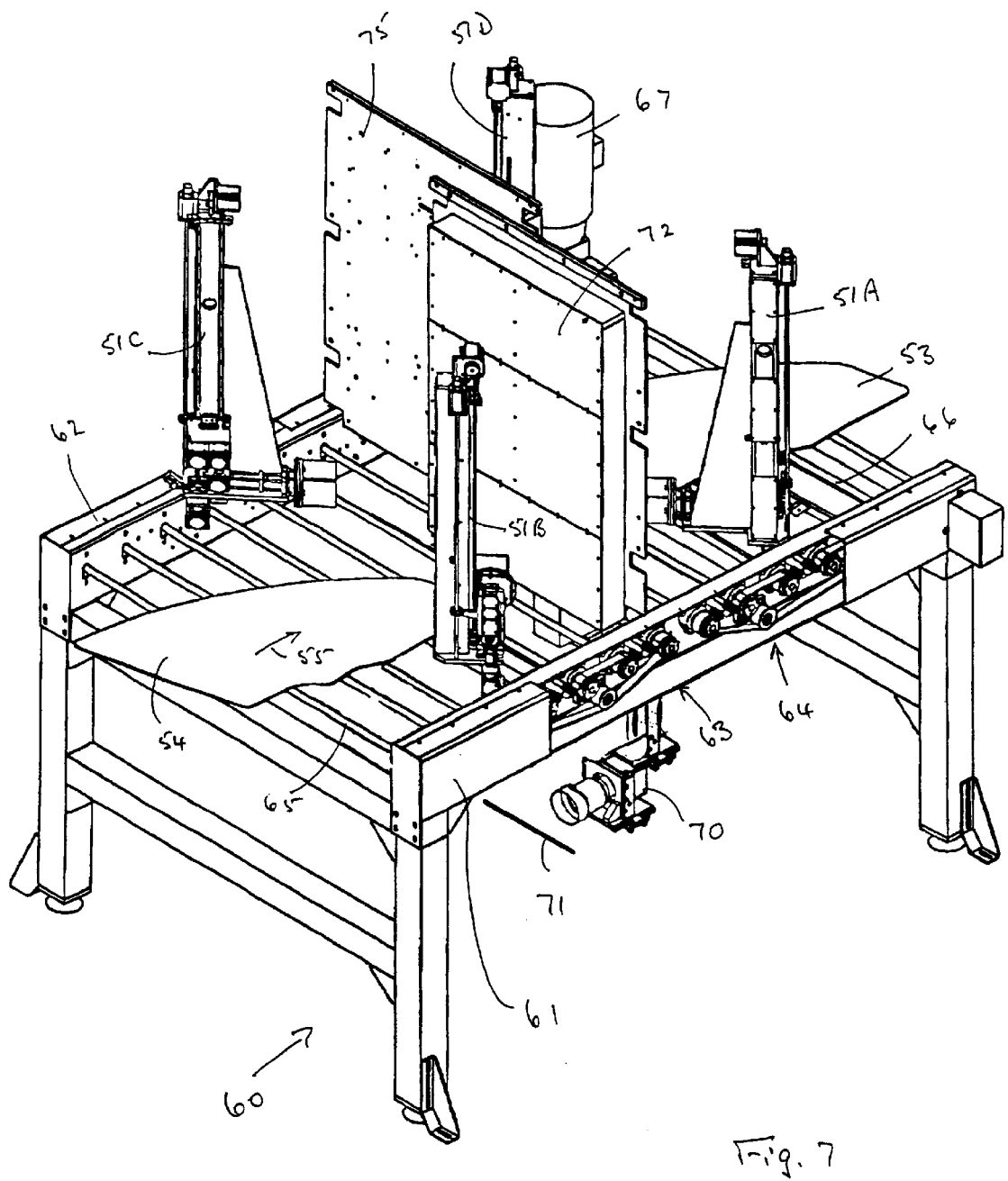
FIG. 7 is a schematic representation of a perspective view of the apparatus of FIG. 6.

FIG. 7 shows a perspective view of the apparatus of FIG. 6. Only viewing area camera 70 is shown in FIG. 7. Drive mechanisms 63 and 64 are shown to have belts around a series of pulleys, to drive rollers 65 and 66.

The present invention provides a glass edge inspection apparatus that is capable of automation, and which utilizes laser optics and a computer vision-based system.

In preferred embodiments of the invention, the combination provides an advanced image analysis with exceptional inspection accuracy e.g. between 50 $\mu$m and 100 $\mu$m, as well as the capability to detect and differentiate a wide variety of defects including edge chips, cracks, shiners, V-chips, burns and other edge defects, and identifies the location, type and magnitude of the defects on the glass. A defective area of the edge surface has different light scattering properties than an edge surface that has been ground properly. In particular, defective areas appear as dark spots i.e. areas of low intensity, whereas a surface that is properly ground gives a bright background i.e. an area of high intensity. Detection and measurement of the size of the dark areas provides information on the location, size and type of the defect. The apparatus is capable of being operated at high-speeds e.g. at line speeds of up to 0.3 m/sec, or higher. Thus, the inspection apparatus may be used in-line in many manufacturing processes.

The software used in the apparatus may be featured with a menu-based graphical user interface for ease of use, pass/fail specification changes and new model set ups, as well as automatic change over and calibration of the apparatus.

In a preferred embodiment, a standard user interface screen with a defect map is used, having coloured icons that represent various types of defects. For examples, circles may be used to represent edge chips, squares to represent V-chips, triangles to represent shiners and so on. The icons may be made to appear at the actual x,y co-ordinates where the defects are located in the sheet of glass. In addition, the icons may be colour coded to represent the size of the defects e.g. the icons could be green to represent a very small defect, yellow to represent a medium defect and red to represent a large defect or reject. Moreover, software may be provided where the user can "click" on any icon to provide characteristics of the defect, including type, size and location. 3-D visualization and mapping of the defects is also possible. Removable surface contaminants such as dust and water, may or may not be not detected by the apparatus, depending on the particular application of the apparatus.

It is to be understood that electronic hardware would be interfaced with the inspection apparatus. This hardware would provide for control of the inspection apparatus, collection of pixel data from the cameras, compression of the data by relaying for further processing only data that is related to areas of interest in the glass sheet, and for pre-processing of pixel data by applying multi-level thresholds and marking transitions between different levels of intensities. A dedicated Peripheral Processor Board (PPB) may be used to further process the data by means of software. The processed data may then be transmitted to a gauge host computer for the purpose of visualization and control, as discussed herein.

The inspection apparatus may be set to recognize a threshold of illumination that indicates the presence of glass. The transitions that pass through the threshold may be presented on a computer display tube.

A sheet of glass cut for a particular end-use, for example the window on the side of an automobile, may be of a complicated shape. The position of the glass within the apparatus is not important, provided that it is located within the width of the laser beam. Moreover, the method of the present invention is capable of being used with curved glass, provided that the edge lays in the plane of the laser beams.

Time delayed integration (TDI) techniques may be used in the detection and analysis of the images that are formed and detected.

In an embodiment of the invention, the stepping motor provides $2 \times 10^4$ steps per revolution of the pulley. The distance of the mirror travel per step provided by the stepping motor is 0.051 mm. The mirror position is up-dated at 0.017 seconds. It is preferred that the mirror motion be up-dated for every 5 mm of travel of the glass. The camera depth of field in the embodiment is ±30 mm and the total path length of the laser beam should be maintained within the depth of field. This may be accomplished by determining the actual mirror position of the movable head by measurement and by calculation based on movement of the glass. The accumulated error between the actual and calculated values should remain within the range of ±30 mm.

As noted above, the location of the glass is tracked as the glass approaches the position of the lasers, for example by counting of encoder pulses. The acceleration of the stepper motor and hence the position of the moveable mirrors is limited. Thus, motion of the mirrors should be commenced at an appropriate time prior to arrival of the glass so that mirror speed and glass edge speed can be matched before scanning commences.

The present invention provides a versatile apparatus and method for inspection of glass, and which is capable of simultaneously identifying a wide variety of defects by type, magnitude and location, in a manner that not only permits identification of glass that does not meet product specification but also assists in identifying the causes of the defects.

The edge inspection apparatus of the present invention may be used in-line with a viewing area inspection system of the type described in the aforementioned Canadian patent application of Weiss and Obotnine.

What is claimed is:

1. A method for the inspection of an edge of a sheet of glass, comprising the steps of:
    a) supporting and moving a sheet of glass in a plane in a first direction, said sheet of glass being maintained in a generally constant plane;
    b) directing a laser beam along an optical path onto said edge of the sheet of glass at an angle to said first direction and directing light reflected from the edge along said optical path to an optical recording device thereby to image said edge, the light reflected from the edge of the sheet of glass being coaxial with the laser beam directed onto the edge of the sheet of glass; and
    c) adjusting the optical path to control the total path length of said laser beam from said laser to said edge and the reflected light from said edge to said optical recording device at a substantially constant length thereby to reduce light intensity variations at said optical recording device resulting from variations in the lateral spacing between said edge and said optical path.

2. The method of claim 1 wherein said adjusting includes moving a housing with mirrors, said laser beam and said reflected light being reflected by the mirrors.

3. The method of claim 2 in which the housing is moved perpendicular to the plane of said sheet of glass.

4. The method of claim 1 in which the sheet of glass is automotive sheet glass.

5. The method of claim 1 in which the sheet of glass is planar.

6. The method of claim 1 in which the sheet of glass is non-planar.

7. The method of claim 1 further comprising the step of displaying detected edge defects on a map showing the location, type and magnitude of said edge defects.

8. The method of claim 7 wherein said edges defects are displayed on said map as selectable icons, the shapes of the icons representing the types of said edge defects and the colors of said icons representing magnitudes of said edge defects.

9. The method of claim 1 wherein steps (b) and (c) are performed on each edge of said sheet of glass.

10. The method of claim 9 in which the sheet of glass is automotive sheet glass.

11. The method of claim 9 in which the sheet of glass is planar.

12. The method of claim 9 in which the sheet of glass is non-planar.

13. An apparatus for inspecting an edge of a sheet of glass, comprising:
    a transport mechanism to support a sheet of glass in a generally constant plane and move said sheet of glass along said plane in a first direction;
    a light source generating an incident beam of laser light;
    an optical path receiving the incident beam from said light source and directing said incident beam onto an edge of said sheet of glass at an angle to said first direction, said optical path further receiving a reflected beam of laser light from said edge, said reflected beam being coaxial with said incident beam;
    an imager receiving said reflected beam thereby to capture images of said edge; and
    an adjustment mechanism adjusting said optical path to maintain the total path length of said incident beam from said light source to said edge and said reflected beam from said edge to said imager at a substantially constant length to reduce light intensity variations at said imager resulting from variations in the lateral spacing between said edge and said optical path.

14. The apparatus of claim 13 in which the sheet of glass is automotive sheet glass.

15. The apparatus of claim 13 in which the sheet of glass is planar.

16. The apparatus of claim 13 in which the sheet of glass is non-planar.

17. The apparatus of claim 13 wherein said optical path includes a set of mirrors and a beamsplitter, said beamsplitter allowing the incident beam from said light source to pass therethrough to said set of mirrors and be reflected by said set of mirrors to said edge, said beamsplitter further directing the reflected beam received from said set of mirrors to said imager, at least some of the mirrors in said set being moveable in response to said adjustment mechanism thereby to maintain said total path length.

18. The apparatus of claim 17 wherein said set of mirrors includes a stationary mirror having a reflecting surface that intersects said plane and a moveable pair of mirrors disposed intermediate said beamsplitter and said stationary mirror, said moveable pair of mirrors being moved by said adjustment mechanism.

19. The apparatus of claim 18 wherein said moveable pair of mirrors changes the direction of said incident beam and said reflected beam by 180° and is moved by said adjustment mechanism in a direction perpendicular to said plane.

20. The apparatus of claim 19 wherein said moveable pair of mirrors is disposed in a housing.

21. The apparatus of claim 13 further comprising a computer communicating with said imager, said computer executing software to determine the location, type and magnitude of defects in the edge of said sheet of glass based on image data captured by said imager.

22. The apparatus of claim 21 wherein said computer records the location, type and magnitude of defects in the edge of said sheet of glass.

23. The apparatus of claim 22 wherein said computer includes a monitor and wherein said software generates a defect map showing the location, type and magnitude of defects in the edge of said sheet of glass for display on said monitor.

24. The apparatus of claim 23 wherein said detected defects are displayed on said map as icons, said icons being selectable to present characteristics of said detected defects.

25. The apparatus of claim 24 wherein the shapes of said icons represent the types of the detected defects.

26. The apparatus of claim 25 wherein the colors of said icons represent the sizes of the detected defects.

27. An inspection system for inspecting edges of a sheet of glass, comprising:
   a transport mechanism to support a sheet of glass in a generally constant plane and move said sheet of glass along said plane in a first direction; and
   a plurality of inspection apparatuses each imaging a respective edge of said sheet of glass, each inspection apparatus including:
      a light source generating an incident beam of laser light;
      an optical path receiving the incident beam from said light source and directing said incident beam onto said respective edge at an angle to said first direction, said optical path further receiving a reflected beam of laser light from said respective edge, said reflected beam being coaxial with said incident beam;
      an imager receiving said reflected beam thereby to capture images of said respective edge; and
      an adjustment mechanism adjusting said optical path to maintain the total path length of said incident beam from said light source to said respective edge and said reflected beam from said respective edge to said imager at a substantially constant length to reduce light intensity variations at said imager resulting from variations in the lateral spacing between said respective edge and said optical path.

28. An inspection system according to claim 27 including four inspection apparatuses.

29. An inspection system according to claim 28 wherein said inspection apparatuses are arranged in a rectangle, the inspection apparatuses at opposite diagonal corners of said rectangle being aligned.

30. The inspection of claim 29 wherein each said optical path includes a set of mirrors and a beamsplitter, said beamsplitter allowing the incident beam from said light source to pass therethrough to said set of mirrors and be reflected by said set of mirrors to said respective edge, said beamsplitter further directing the reflected beam received from said set of mirrors to said imager, at least some of the mirrors in said set being moveable in response to said adjustment mechanism thereby to maintain said total path length.

31. The inspection system of claim 30 wherein said set of mirrors includes a stationary mirror having a reflecting surface that intersects said plane and a moveable pair of mirrors disposed intermediate said beamsplitter and said stationary mirror, said moveable pair of mirrors being moved by said adjustment mechanism.

32. The inspection system of claim 31 wherein said moveable pair of mirrors changes the direction of said incident beam and said reflected beam by 180° and is moved by said adjustment mechanism in a direction perpendicular to said plane.

33. The inspection system of claim 32 wherein said moveable pair of mirrors is disposed in a housing.

34. The inspection system of claim 27 further comprising a computer communicating with said imagers, said computer executing software to determine the location, type and magnitude of defects in the edges of said sheet of glass based on image data captured by said imagers.

35. The inspection system of claim 34 wherein said computer records the location, type and magnitude of defects in the edges of said sheet of glass.

36. The inspection system of claim 35 wherein said computer includes a monitor and wherein said software generates a defect map showing the location, type and magnitude of defects in the edges of said sheet of glass for display on said monitor.

37. The inspection system of claim 36 wherein said detected defects are displayed on said map as icons, said icons being selectable to present characteristics of said detected defects.

38. The inspection system of claim 37 wherein the shapes of said icons represent the types of the detected defects.

39. The inspection system of claim 38 wherein the colors of said icons represent the sizes of the detected defects.

40. The inspection system of claim 27 in which the sheet of glass is automotive sheet glass.

41. The inspection system of claim 27 in which the sheet of glass is planar.

42. The inspection system of claim 27 in which the sheet of glass is non-planar.

* * * * *